United States Patent
Hirokawa (10) Patent No.: US 9,430,692 B2
(45) Date of Patent: Aug. 30, 2016

(54) FINGERPRINT MINUTIA DISPLAY INPUT DEVICE, FINGERPRINT MINUTIA DISPLAY INPUT METHOD, AND FINGERPRINT MINUTIA DISPLAY INPUT PROGRAM

(71) Applicant: NEC Solution Innovators, Ltd., Tokyo (JP)

(72) Inventor: Akira Hirokawa, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 0 days.

(21) Appl. No.: 14/402,458

(22) PCT Filed: May 21, 2013

(86) PCT No.: PCT/JP2013/064098
§ 371 (c)(1),
(2) Date: Nov. 20, 2014

(87) PCT Pub. No.: WO2013/176134
PCT Pub. Date: Nov. 28, 2013

(65) Prior Publication Data
US 2015/0161431 A1    Jun. 11, 2015

(30) Foreign Application Priority Data
May 22, 2012    (JP) .................................. 2012-116565

(51) Int. Cl.
*G06K 9/00*    (2006.01)
*A61B 5/117*    (2016.01)

(52) U.S. Cl.
CPC ......... *G06K 9/00067* (2013.01); *A61B 5/1172* (2013.01); *G06K 9/00013* (2013.01); *G06K 9/00033* (2013.01); *G06K 9/00073* (2013.01)

(58) Field of Classification Search
None
See application file for complete search history.

(56) References Cited

U.S. PATENT DOCUMENTS

| 5,524,161 | A | * | 6/1996 | Omori | ................ | G07C 9/00158 |
| | | | | | | 382/125 |
| 2007/0237392 | A1 | * | 10/2007 | Ohara | .................. | H04N 1/4074 |
| | | | | | | 382/171 |
| 2008/0226143 | A1 | * | 9/2008 | Hara | ........................ | G06K 9/03 |
| | | | | | | 382/125 |

FOREIGN PATENT DOCUMENTS

| JP | 4-306778 | 10/1992 |
| JP | 2001-344604 | 12/2001 |
| JP | 2007-267188 | 10/2007 |
| JP | 2008/225764 | 9/2008 |

OTHER PUBLICATIONS

International Search Report mailed Aug. 13, 2013 in corresponding PCT International Application.

* cited by examiner

*Primary Examiner* — Kim Vu
*Assistant Examiner* — Fred Hu
(74) *Attorney, Agent, or Firm* — Finnegan, Henderson, Farabow, Garrett & Dunner LLP (57) ABSTRACT

A fingerprint minutia display input device includes: an image output controller for displaying a fingerprint image and a pointer for designating a minutia; and a minutia input setting unit for displaying a minutia display mark on the minutia; wherein the fingerprint minutia display input device includes a gray-scale value adjustment unit for setting the gray-scale intensity of the entire fingerprint image on which the pointer is positioned, the setting being performed within a range of a display gray-scale width constituted with upper-limit and lower-limit gray-scale values. The screen output controller includes a gray-scale width update function for displaying an updated output display of the fingerprint image in the set display gray-scale width, and a gray-scale width fixing/holding function for fixedly holding the set display gray-scale width as a set display gray-scale width for the minutia display input when there is no new setting information regarding the display gray-scale width.

20 Claims, 8 Drawing Sheets

POINTER POSITIONS AND CLARIFIED LATENT FINGERPRINTS

POINTER POSITIONS AND CLARIFIED LATENT FINGERPRINTS

UNCLEAR LATENT FINGERPRINT

FIG. 6

ADJUSTMENT OF GRAY-SCALE VALUE WIDTH
(GRAY-SCALE VALUES OF 0 - 255 ARE LINEARLY
CONVERTED TO 237 - 254 IN THIS CASE)

EXAMPLES OF CLEAR/UNCLEAR AREAS

FINGERPRINT MINUTIA DISPLAY INPUT DEVICE, FINGERPRINT MINUTIA DISPLAY INPUT METHOD, AND FINGERPRINT MINUTIA DISPLAY INPUT PROGRAM

CROSS-REFERENCE TO RELATED PATENT APPLICATIONS

This application is a National Stage Entry of International Application No. PCT/JP2013/064098, filed May 21, 2013, which claims priority from Japanese Patent Application No. 2012-116565, filed May 22, 2012. The entire contents of the above-referenced applications are expressly incorporated herein by reference.

TECHNICAL FIELD

The present invention relates to a fingerprint minutia display input device, a fingerprint minutia display input method, and a fingerprint minutia display input program for inputting minutia display information at positions corresponding to minutiae contained in a latent fingerprint within a fingerprint image.

BACKGROUND ART

Figure 5:
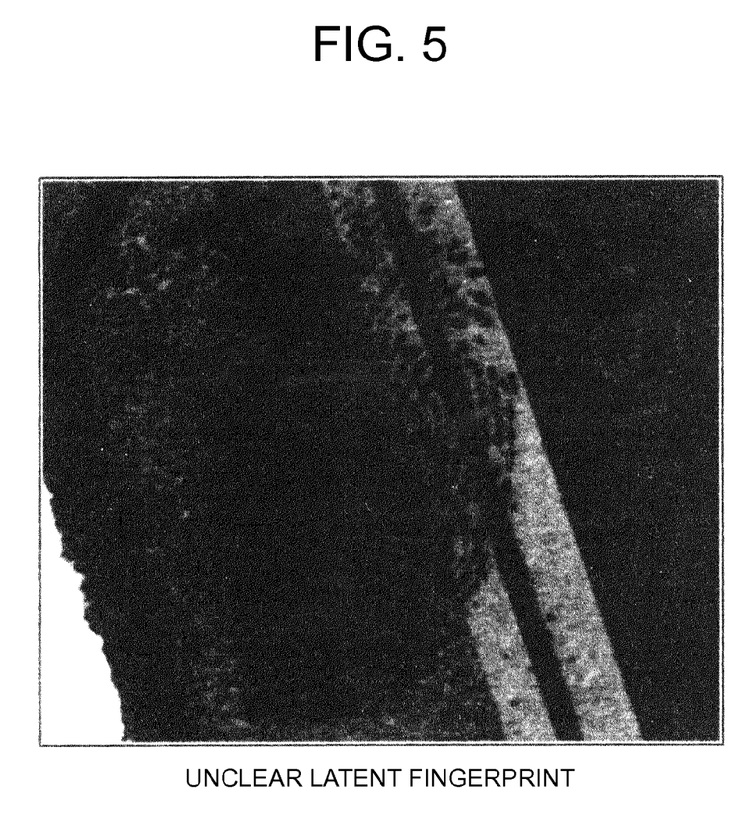
FIG. 5 is an explanatory image showing an example of a latent fingerprint image that is an input target of the minutia information by the fingerprint minutia input device disclosed in FIG. 1.

As shown in FIG. 5, the minutia information input device which executes setting of minutia information on the minutiae contained in a latent fingerprint within a fingerprint image may deal with a fingerprint image including an unclear latent fingerprint in some cases.

With the minutia information input device in general, operations for inputting and designating positions of minutiae included in a latent fingerprint are executed by an operator.

Figure 6:
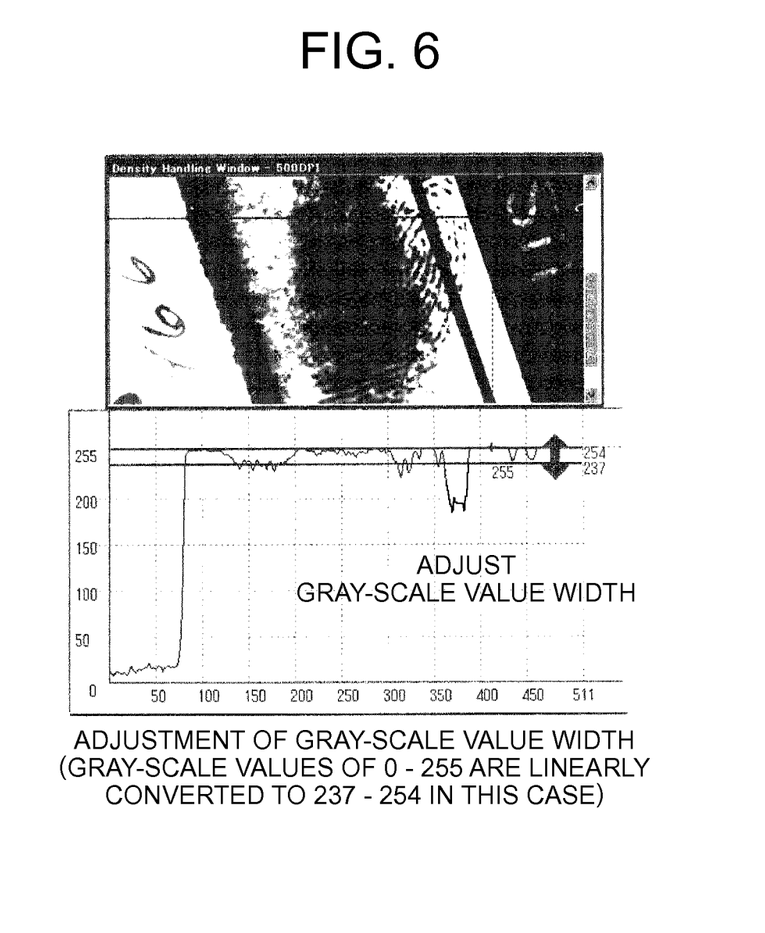
FIG. 6 is an explanatory image showing the result acquired by performing the adjustment processing (clarification processing) of the gray-scale value width on the latent fingerprint image shown in FIG. 5 based on the gray-scale value width inputted by an operator.
Figure 7:
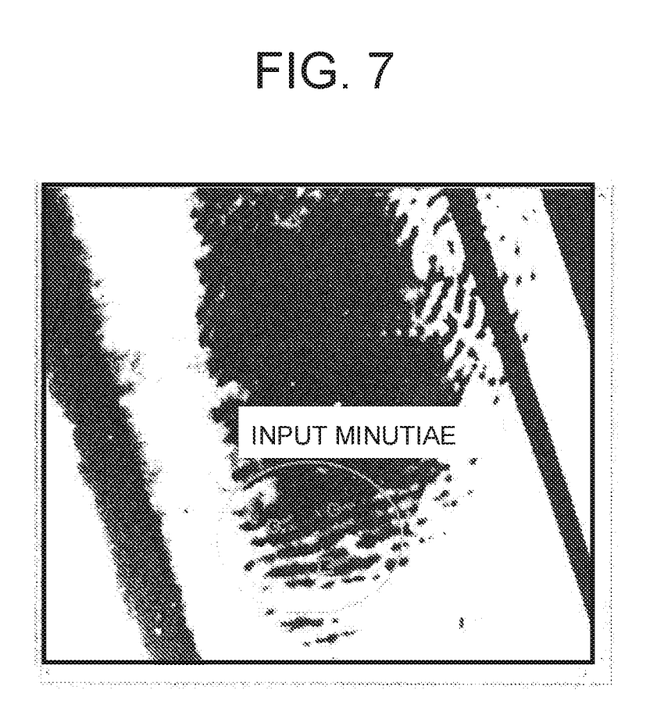
FIG. 7 is an explanatory image showing an example of a case where the minutia information is inputted to the latent fingerprint image of FIG. 6.

In a case of inputting minutia information for an unclear latent fingerprint, first, the operator performs gray-scale value width adjusting processing on the entire fingerprint image to make the latent fingerprint clear as shown in FIG. 6, and then inputs the minutia information as shown in FIG. 3. Note here that the minutia information including minutia positions, minutia directions, and minutia types for each minutia is set for each minutia (FIG. 7). As the minutia information, it is also possible to employ the setting for executing only plotting input for showing the positions of the minutiae.

Figure 8A:
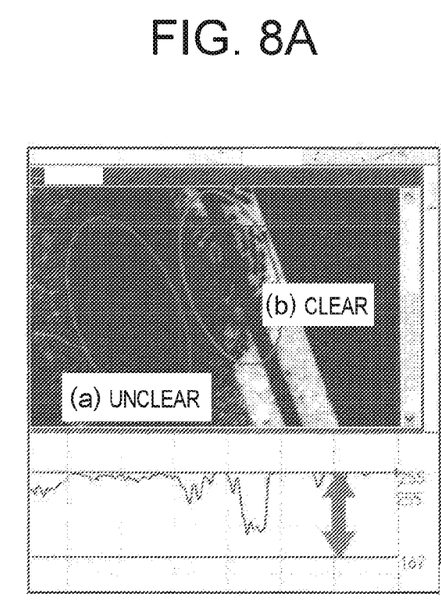
FIG. 8A, FIG. 8B, and FIG. 8C are explanatory images, each showing the result acquired by performing the adjustment processing (clarification processing) of the gray-scale value width on the latent fingerprint image shown in FIG. 1 based on the gray-scale value width inputted by the operator.

As described, in a case where the clarification processing is executed on the entire fingerprint image and then the minutia information is inputted, normally, as shown in FIG. 8A, the optimum gray-scale value width utilized for acquiring distinctiveness varies depending on the region of the fingerprint image or the area of the latent fingerprint.

Note here that the latent fingerprint in (a) region of the fingerprint image in FIG. 8A is so unclear that the finger ridgeline shape cannot be recognized, while the ridgeline shape of the latent fingerprint in (b) region appears clearly. The fingerprint image shown in FIG. 8A is outputted and displayed with the display gray-scale width by setting the upper limit value as 255 and the lower limit value as 167, for example.

In such case, the operator clarifies the fingerprint image through setting the gray-scale width (dynamic range) by corresponding to each of the areas of different distinctiveness in the latent fingerprint and inputs the minutia information for the latent fingerprint in the partial region (image region) of high distinctiveness in each of the partial regions.

Figure 8B:
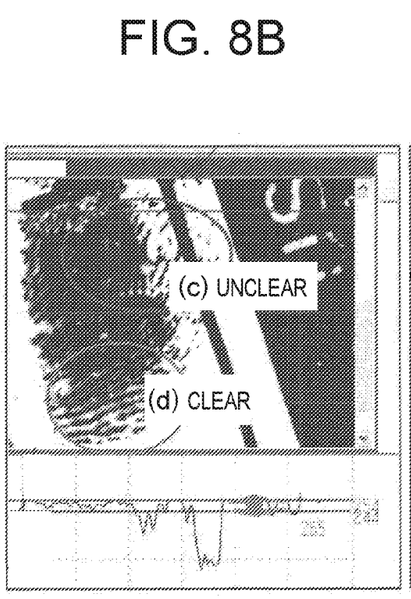

For example, FIG. 8B shows the state where the gray-scale value width (dynamic range) in the fingerprint image of FIG. 8A is adjusted to be narrowed to "upper limit value 254, lower limit value 244" from "upper limit value 255, lower limit value 167". As a result, in (d) region, the ridgeline shape of the latent fingerprint appears clearly.

In the meantime, in (c) region as a result of the adjusting processing, a part of the fingerprint ridgeline is white and cannot be observed. Thereby, it becomes a region that is so unclear that the accurate shape of the latent fingerprint cannot be grasped.

Figure 8C:
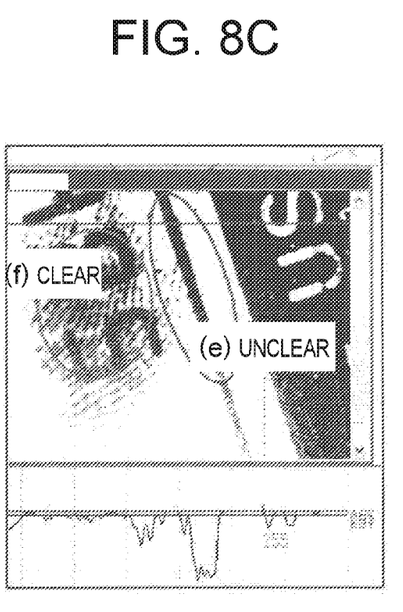

Further, FIG. 8C shows the state where the gray-scale value width (dynamic range) in the fingerprint image of FIG. 8B is adjusted to be narrowed to "upper limit value 254, lower limit value 251" from "upper limit value 255, lower limit value 167". As a result of the adjustment, in (f) region, the ridgeline shape of the latent fingerprint appears clearly.

In the meantime, in (e) region as a result of the adjusting processing, a part of the fingerprint ridgeline is white and cannot be observed. Thereby, it becomes a region that is so undistinctive that the correct shape of the latent fingerprint cannot be grasped.

As described, for clarifying the fingerprint image, it is necessary to repeatedly perform the image clarification processing and the minutia input processing at least twice or more for each image region. Thus, in a case of setting the minutia information for a fingerprint image containing a great amount of minutiae or for a great amount of fingerprint images, the number of operation steps and the operation time for the minutia input operation become enormous.

In particular, as described above, there are a large number of steps contained in the operation steps such as performing screen transition by activating a graph showing a histogram of an image from a fingerprint image for adjusting the gray-scale value width in the fingerprint image, adjusting the gray-scale value width on the graph, then activating the fingerprint image screen on which the gray-scale value width is reflected again, and plotting the minutia information. This is troublesome for the operator, and the terminal operation time becomes extremely long.

As a related technique thereof, there is known a fingerprint collation system (Patent Document 1) which: generates fingerprint data containing information regarding minutiae for each fingerprint image; sets minutia information such as positions of the minutiae, the minutia directions, and the like by specifying a common minutia that is a same minutia from the corresponding relations of the minutiae between a plurality of pieces of fingerprint data; and performs fingerprint matching based on synthesized fingerprint data generated based on the minutia information.

Patent Document 1: Japanese Unexamined Patent Publication 2001-344604

However, as evident from the disclosed content thereof, the related technique disclosed in Patent Document 1 described above cannot be applied for fingerprint images including unclear latent fingerprints. Thus, the related technique always requires input operations of the minutia information done by the operator, which is troublesome.

It is an object of the present invention to improve the inconveniences of the related technique described above and to provide a fingerprint minutia display input device, a fingerprint minutia display input method, and a fingerprint minutia display input program, which make it possible for the operator to quickly and simply perform display operations for each minutia position in a fingerprint image.

DISCLOSURE OF THE INVENTION

In order to achieve the foregoing object, the fingerprint minutia input device according to the present invention is a fingerprint minutia input device including a main device body which includes: an image output controller which outputs/displays a fingerprint image containing fingerprint ridgelines and a pointer for designating a coordinate position of a minutia of the fingerprint image on a display screen (monitor); and a minutia input setting unit which sets/displays a minutia display mark for the minutia on the fingerprint image designated by the pointer according to an external command, wherein:

the main device body includes a gray-scale value adjustment unit which sets gray-scale intensity of the entire fingerprint image where the pointer is located to be used for gray-scale adjustment within a display gray-scale range constituted with a gray-scale upper limit value and a gray-scale lower limit value according to an external command; and the screen output controller includes a gray-scale width update function which updates/outputs output display of the fingerprint image with the display gray-scale width set anew by the gray-scale value adjustment unit when setting/displaying the minutia display mark, and a gray-scale width fixing/holding function which fixes and holds the set display gray-scale width as the display gray-scale width for displaying/inputting the minutia when there is no new setting information of the display gray-scale width from the gray-scale value adjustment unit.

Further, in order to achieve the foregoing object, the fingerprint minutia input method according to the present invention is characterized to be used for the fingerprint minutia input device including a main device body which includes an image output controller which outputs/displays a fingerprint image containing fingerprint ridgelines and a pointer for designating a coordinate position of a minutia of the fingerprint image on a display screen (monitor) and a minutia input setting unit which sets/displays a minutia display mark for the minutia on the fingerprint image designated by the pointer according to an external command, and the method includes:

selecting and setting gray-scale intensity of the entire fingerprint image where the pointer is located to be used for gray-scale display within a display gray-scale range constituted with a gray-scale upper limit value and a gray-scale lower limit value from a memory provided in advance by the gray-scale value adjustment unit of the main device body according to an external command (a gray-scale intensity selecting/setting step);

then, updating/outputting output display of the fingerprint image by the screen output controller with the display gray-scale width selected and set anew by the gray-scale value adjustment unit when setting/displaying the minutia display mark (a gray-scale width update processing step);

subsequently, fixing and holding the set display gray-scale width as the display gray-scale width for displaying/inputting the minutia when there is no new setting information of the display gray-scale width from the gray-scale value adjustment unit (a gray-scale width fixing/holding step); and thereafter, setting/displaying the minutia display mark for the minutia of the fingerprint image fixedly set with the display gray-scale width by the minutia input setting unit according to an external command (a display mark setting/displaying step).

Furthermore, in order to achieve the foregoing object, the fingerprint minutia input program used according to the present invention is characterized to be used for a fingerprint minutia input device including a main device body which includes an image output controller which outputs/displays a fingerprint image containing fingerprint ridgelines and a pointer for designating a coordinate position of a minutia of the fingerprint image on a display screen (monitor) and a minutia input setting unit which sets/displays a minutia display mark for the minutia on the fingerprint image designated by the pointer according to an external command, and the program causes a computer provided to the main device body to execute each of:

a display gray-scale value acquiring function which selectively takes out gray-scale intensity of the entire fingerprint image where the pointer is located to be used for gray-scale display within a display gray-scale width range constituted with a gray-scale upper limit value and a gray-scale lower limit value from a memory provided in advance additionally according to an external command;

a gray-scale width updating/displaying function which updates/outputs output display of the entire fingerprint image with the display gray-scale width selected anew when setting/displaying the minutia display mark;

a gray-scale width fixing/holding function which fixes and holds the set display gray-scale width as the display gray-scale width for displaying/inputting the minutia when there is no new setting information of the display gray-scale width; and a display mark setting processing function which sets/displays a display mark for the minutia of the fingerprint image fixedly set with the display gray-scale width according to an external command.

The present invention is structured in the manner described above, which includes the image output controller which gray-scale-displays the pointer position coordinate of a fingerprint image on the display screen with the gray-scale upper limit value and the lower limit value of the variably settable gray-scale value width. Therefore, it is possible to provide the fingerprint minutia display input device, the fingerprint minutia display input method, and the fingerprint minutia display input program, which make it possible for the operator to quickly and simply perform display input operations for each minutia position in a fingerprint image.

BEST MODES FOR CARRYING OUT THE INVENTION

Embodiment

Hereinafter, an embodiment of the present invention will be described by referring to the accompanying drawings.

The basic structural content of a fingerprint minutia input device 1 of the embodiment will be described first, and specific content will be described thereafter.

Figure 1:
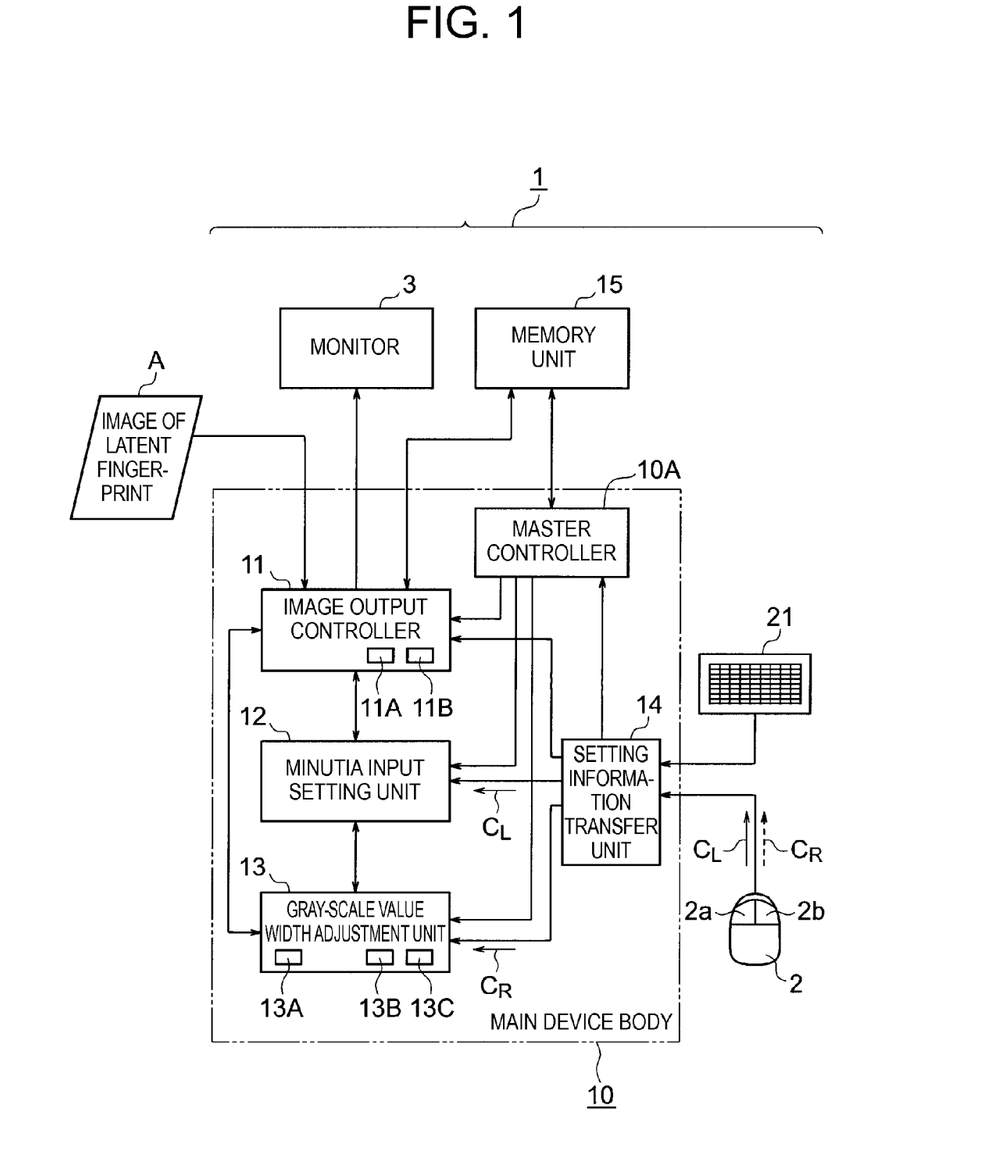
FIG. 1 is a block diagram showing an example of a fingerprint minutia input device according to the embodiment.

First, as shown in FIG. 1, the fingerprint minutia input device 1 according to the embodiment includes: an image output controller 11 which outputs/displays fingerprint image data inputted from outside on a monitor 3 that is a data display module; a minutia input setting unit 12 which inputs minutia position information showing minutiae of corresponding coordinate positions on the fingerprint image based on input data inputted by an operator from an input apparatus (e.g., a mouse); a gray-scale value width adjustment unit 13 which sets the display gray-scale value width (dynamic range) of the fingerprint image outputted/displayed by the image output controller 11 by corresponding to the input operation content done through the input apparatus 2; and a setting information transfer unit 14 which, when there is input information containing an operation command from outside for each of the image output controller 11, the minutia input setting unit 12, and the gray-scale value width adjustment unit 13, transfers the setting content set/inputted via the input apparatus 2 to each of the corresponding structural parts.

In this embodiment, a main device body 10 is constituted with the image output controller 11, the minutia input setting unit 12, the gray-scale value width adjustment unit 13, and the setting information transfer unit 14. The main device body 10 is provided with a memory unit 15 for storing/holding fingerprint images inputted in advance. Further, a reference numeral 21 shows a keyboard as another input apparatus. Furthermore, this embodiment uses an actual latent fingerprint image A as the fingerprint image.

As a whole, the minutia information input device 1 according to the embodiment is a computer device which includes the memory unit 15 such as a memory (flash memory, hard disk drive, etc.) and a CPU (master controller 10A) which performs execution processing of programs set in advance to the memory unit 15 as the inner structure. The device 1 uses the main device body 10 as the main part and further includes the mouse 2 and the keyboard 21 as the input apparatuses and the monitor 3 as a display screen (data display module) for outputting the processing content.

The above-described mouse 2 that is the input apparatus provided to the fingerprint minutia input device 1 includes a left button as a left click part 2a and a right button as a right click part 2b (hereinafter, "input apparatus 2" is referred to as "mouse 2").

Note here that the left click part 2a of the mouse 2 includes a display command input function which externally inputs a minutia display command $C_L$ of a minutia display mark to the minutia input setting unit 12 by a click operation of the left click part 2a. Further, the right click part 2b of the mouse 2 includes a gray-scale display range setting function which sets/inputs the gray-scale display upper limit value and lower limit value of the fingerprint image to the gray-scale value width adjustment unit 13 by a click operation of the right click part 2b as gray-scale intensity information $C_R$ by successively making selections while moving the mouse 2. The gray-scale intensity information $C_R$ also functions as a startup signal for the gray-scale value width adjustment unit 13.

Further, the setting information transfer unit 14 which transfers each setting information inputted from each of the left and right click parts 2a, 2b of the mouse 2 includes: a first transfer processing function which, when coordinate position information of the moved destination of the mouse pointer (pointer/arrow set on the display screen by the mouse 2) on the fingerprint image A is set/inputted by corresponding to the move amount of the mouse 2, transfers it to the image output controller 11; and a second transfer processing function which, when the gray-scale intensity information regarding the display gray-scale width in which the upper limit value and the lower limit value of the image display gray-scale intensity are specified is set/inputted via the right click part 2b of the mouse 2, transfers it to the gray-scale value width adjustment unit 13.

Further, the setting information transfer unit 14 includes a third transfer processing function which performs transfer processing of the minutia display command $C_L$ to the minutia input setting unit 12 when the minutia display command $C_L$ of the minutia on the fingerprint image A is set/inputted to the minutia input setting unit 12 via the left click part 2a of the mouse 2 while the gray-scale intensity information is being set/inputted via the right click part 2b of the mouse 2.

Note here that the image output controller 11 outputs/displays the inputted fingerprint image on the monitor 3 in advance and outputs/displays the mouse pointer on that image.

Further, the image output controller 11 includes a function which outputs/displays the fingerprint image on the monitor 3 with the display gray-scale width (dynamic range) in which the gray-scale upper limit value (gray-scale upper value) and the lower limit value (gray-scale lower value) converted by the gray-scale value width adjustment unit 13 are taken as the upper limit value and the lower limit value.

Further, the image output controller 11 includes a gray-scale width updating/displaying function (gray-scale width update function) 11A which updates/displays the dynamic range of the fingerprint image outputted/displayed on the monitor 3 with the display gray-scale width determined with the gray-scale upper limit value and the lower limit value informed anew by the gray-scale value width adjustment unit 13. Furthermore, the image output controller 11 includes a gray-scale width fix-setting function 11B which fixes and sets the display data regarding the display gray-scale width outputted/displayed on the monitor 3 at the point where the display gray-scale width fixing command information set in advance is acquired from the mouse 2.

The minutia input setting unit 12 of this embodiment is structured to perform display/input of the minutia of the fingerprint image on the display screen of the monitor 3 via the image output controller 11 when specific information (minutia display command $C_L$) is inputted by a click operation of the left click part 2a of the mouse 2.

Further, the minutia input setting unit 12 is structured to set/input the display of the minutia for the fingerprint image when the display gray-scale width is fixedly set by the image output controller 11 (a fixed gray-scale width minutia input function).

The fixed gray-scale width minutia input function is executed by a click operation (left click) of the left click part 2a of the mouse 2 by the operator as described above.

In this case, the minutia input setting unit 12 may be structured to be capable of inputting the minutia directions and the minutia types as the minutia information in addition to the positional information of the minutiae.

Further, the minutia input setting unit 12 in this embodiment is set to store/hold the information (minutia positional information/minutia mark) showing the position of the minutia by corresponding to the position of the pointer on the screen when a left click is done on the mouse 2.

In the meantime, the gray-scale value width adjustment unit 13 includes a gray-scale value notifying function 13B which converts the display position coordinate of the mouse pointer to the gray-scale upper limit value and the lower limit value and informs the converted gray-scale upper limit value and lower limit value to the image output controller 11.

Hereinafter, the operating functions of the image output controller 11, the minutia input setting unit 12, and the gray-scale value width adjustment unit 13 will be described in more details.

The minutia setting unit 12 performs input of the minutia display information (minutia display input function) when the left click part 2a of the mouse 2 is clicked (left click) and, upon that, the image output controller 11 (as shown in FIG. 7) controls display of drawing which shows the minutia on the screen of the monitor 3 (the minutia is displayed/inputted).

As shown in FIG. 7, on the fingerprint image A outputted on the monitor 3, the mouse pointer whose point position changes according to the move amount of the mouse is displayed. The mouse operation of this case is executed by the operator.

In the meantime, the gray-scale value width adjustment unit 13 includes a gray-scale value width adjusting function 13C which starts the adjusting function of the gray-scale value width (dynamic range) upon detecting that the operator pressed the right click part 2b of the mouse 2 (or a prescribed key on the keyboard 21 set in advance). The reference code $C_R$ also functions as a startup signal for the gray-scale value width adjustment unit 13 outputted by a pressing operation (right click) of the right click part 2b by the operator.

At this time, the gray-scale value width adjustment unit 13 sets a region (effective range region P) having prescribed length coordinate axes in the horizontal direction and the perpendicular direction on the monitor screen from a reference position provided that the position on the screen when the right click part 2b is pressed (right-clicked) is taken as the reference position.

Figure 2:
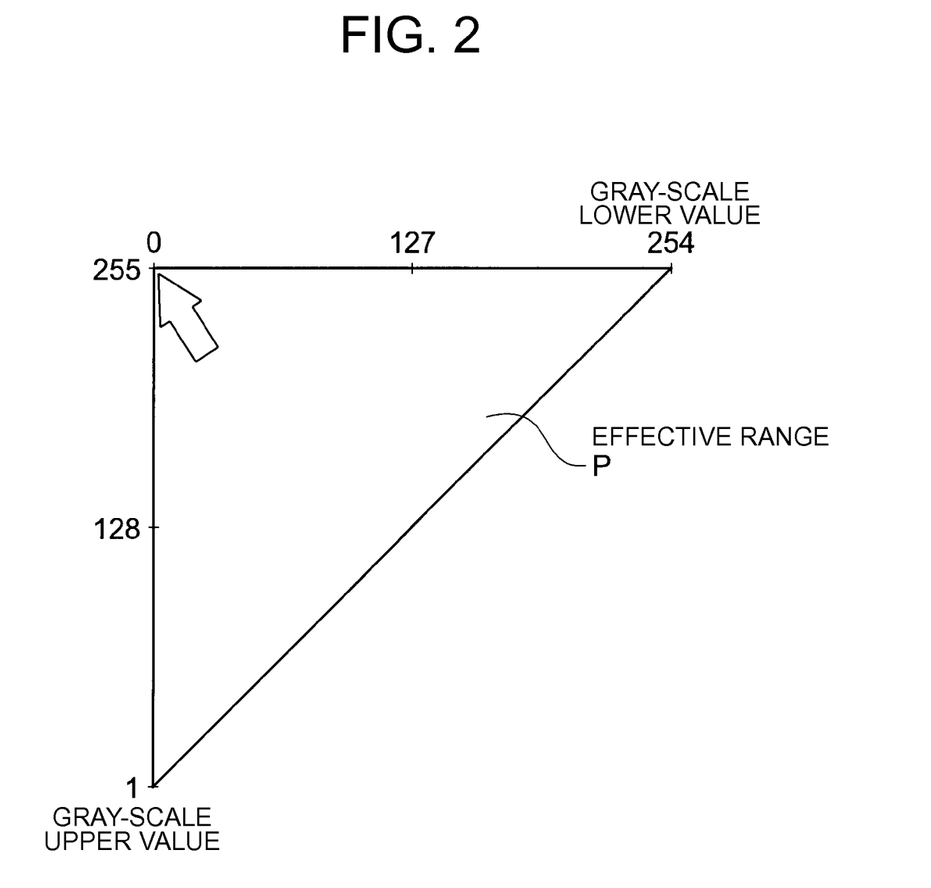
FIG. 2 is an explanatory chart showing examples of gray-scale lower limit value, gray-scale upper limit value, and effective range defined virtually by taking mouse pointer positions on a latent fingerprint image as the reference value in the fingerprint minutia input device according to the embodiment.

The effective range region P having such coordinate axes specifically shows a right triangular region as shown in FIG. 2, for example.

Specifically, the effective range region P is defined as a region of an inside part (including the boundary) of a right triangle which is constituted with a lateral axis of a coordinate value from 0 as the reference position to 254, for example, in the horizontal wide range direction, a longitudinal axis of a coordinate value from 255, for example, as the reference position to 0 in the perpendicular direction, and a straight line having the lower end of the longitudinal axis and the right end of the lateral axis as its both ends. Further, within the region, each of the gray-scale lower value and the gray-scale upper value is defined to satisfy "gray-scale lower value<gray-scale upper value".

The effective range region P shown in FIG. 2 (and the numerical values showing the coordinate of the effective range region P, etc.) is a layer virtually superimposed and set on the fingerprint image on the screen, and it is not displayed on the actual monitor screen (monitor 3) on which the fingerprint image A is outputted.

The gray-scale value width adjustment unit 13 includes a function which informs the coordinate information within the effective range P as the gray-scale upper value and the gray-scale lower value to the image output controller 11 in a case where the effective range is set by taking the position of the pointer as the reference position (FIG. 2) at the point where a signal (right click) from the right click part 2b of the mouse 2 is detected and then an operation for moving the pointer on the monitor screen within the effective range P is executed in a right-drag state of the mouse 2.

Note here that the gray-scale value width adjustment unit 13 includes a gray-scale value memory 13A which stores a plurality of stages of gray-scale lower limit values in which the values of the gray-scale lower limit values of the fingerprint image A change successively and a plurality of stages of gray-scale upper limit values in which the values of the gray-scale upper limit values of the fingerprint image A change successively.

In the gray-scale value memory 13A, a plurality of stages of respective lower limit values for the single upper limit value are stored to be continuously and successively selectable in response to an external command.

Further, the image output controller 11 includes a function which display-controls the gray-scale value regarding each of the entire points constituting the fingerprint image A outputted on the monitor 3 with the dynamic range in which the gray-scale upper value and the gray-scale lower value sent from the gray-scale value width adjustment unit 13 are taken as the upper limit value and the lower limit value.

That is, when the operator moves the mouse pointer displayed on the monitor 3 in all directions within the effective range P by moving the mouse 2 by right drag, the input data (positional information) is changed and the gray-scale value width adjustment unit 13 can variably output the dynamic range of the gray-scale values of the entire fingerprint image by corresponding to the change.

Specifically, when the pointer (arrow) on the display screen of the monitor 3 moves within the effective range P while the mouse 2 is in a right-drag state, the gray-scale value width adjustment unit 13 determines each of the gray-scale upper value and the lower value corresponding to the position coordinate (position coordinate within the effective range P) of the mouse pointer (white arrow in FIG. 2) and transmits the gray-scale upper value and the lower value to the image output controller 11.

The image output controller 11 outputs/displays the fingerprint image on the monitor 3 with the dynamic range (gray-scale width) having the gray-scale upper value and the lower value as the upper limit value and the lower limit value.

Thereby, the operator can adjust the display dynamic range (display gray-scale range) of the latent fingerprint image outputted/displayed on the monitor 3 through moving the mouse 2 (dragging to the right) while pressing down the right button (right click part 2b).

Further, the image output controller 11 fixes the display dynamic range (display gray-scale value) of the fingerprint image outputted/displayed on the monitor 3 at the point when it is detected that the right-drag state is released (the right-button pressed state is released).

That is, because the right-drag state is released, the gray-scale upper value and the lower value are not sent from the gray-scale value width adjustment unit 13 to the image output controller 11. Therefore, the display dynamic range of the fingerprint image outputted to the monitor 3 is not updated but fixed.

In this case, the image output controller 11 starts the gray-scale width update function 11A at the timing of the input of a minutia display command to update/display the output/display of the fingerprint image with the gray-scale width set anew by the gray-scale value width adjustment unit 13 when the minutia display command from the operation command transfer unit 14 for the minutia input setting unit 12 is inputted, and starts the gray-scale width fixing/holding function 11B to fixedly set/control the display gray-scale width regarding the update display when the input of the minutia display command is released.

Further, in this case, the operator can input the minutiae for the fingerprint image by performing a pressing operation of the left click part 2a (left click) of the mouse 2 while the display gray-scale value of the fingerprint image is being fixed.

Thereby, for example, through fixing the display gray-scale value (i.e., releasing the right-drag state) in a state where the latent fingerprint A in the region near the mouse pointer in the fingerprint image displayed on the monitor 3 is most clarified, the operator can perform a plotting operation of the minutiae in a state where the latent fingerprint is displayed with the highest visibility for the operator oneself.

The operator plots the minutiae through performing left-click in the manner described above. Further, as described above, the gray-scale value width adjusting function 13C is started by pressing down the right button, and the display gray-scale value width is fixed by releasing the right-drag (pressed state of the right click part 2b).

Therefore, the operator moves the pointer on the screen by performing right-drag in a state where the left-click can be done at all times (a finger is placed on the left button) so that the adjusting operation of the gray-scale value width can be done thereby.

Normally, the distinctiveness of the fingerprint varies depending on the image regions in the fingerprint image including the latent fingerprint and the like so that the optimum gray-scale value width also varies for each of the image regions. However, with this embodiment, it is possible to display the fingerprint image with the dynamic range of the highest visibility for the operator in each of the pointer moved destiny regions on the monitor screen. Thus, it is possible to input the minutiae for the latent fingerprint in which each of the image regions is clarified in the optimum manner.

Further, when detecting a pressing signal (right click) from the right click part 2b of the mouse 2 in a state where the display gray-scale width of the fingerprint image outputted/displayed on the monitor 3 is fixed, the image output controller 11 releases the state where the display gray-scale is fixed and sets the fingerprint image to a state to be outputted/displayed under a state where the display gray-scale width is unadjusted.

When the display gray-scale width fixedly set state is released, the image output control module 11 updates the gray-scale width by taking the display gray-scale width when the fingerprint image displayed on the monitor 3 is being fixedly set as the initial display gray-scale width. Thereby, even when the fixedly set state is released, display can be done without rapidly changing the display dynamic range of the fingerprint image. When the display dynamic range of the fingerprint image is returned to the initial gray-scale width of 0-255 because the fixedly set state is released, the fingerprint image to be displayed becomes radically darkened or brightened. This may be hard on the eyes of the operator who is executing the input operation.

Here, the gray-scale width changing state in the fingerprint image when the mouse pointer moves within the effective range while being right-dragged will be described in a specific manner by referring to FIGS. 3A, B, and C.

Figure 3A:
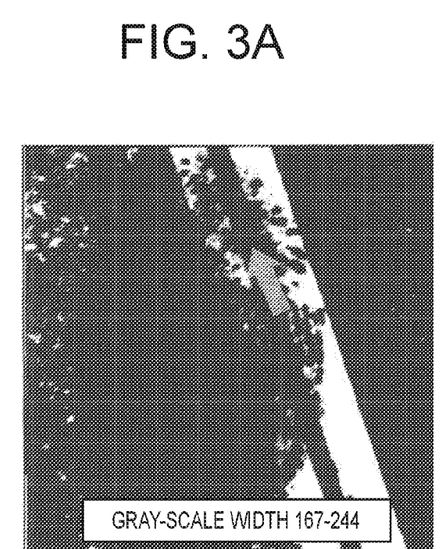
FIG. 3A, FIG. 3B, and FIG. 3C are explanatory images, each showing a fingerprint image on which clarification processing is done by using the display gray-scale value width set based on the mouse pointer position coordinate.
Figure 3B:
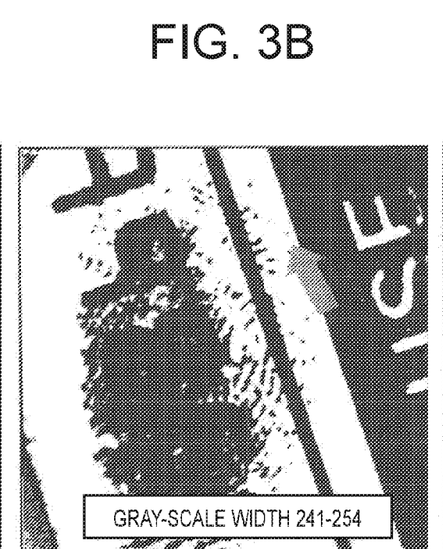
Figure 3C:
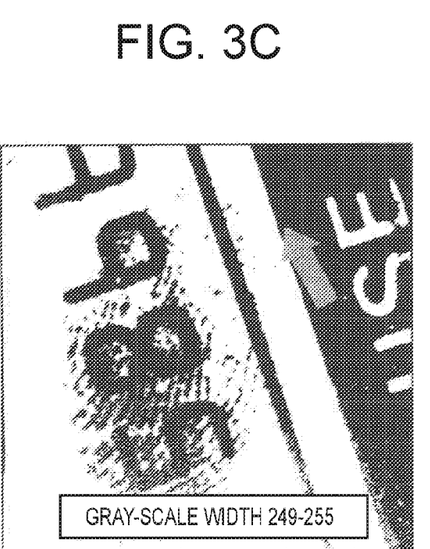

Each of FIGS. 3A, B, and C shows a fingerprint image on which clarification processing is performed with the gray-scale upper and lower values based on those gray-scale upper and lower values (gray-scale width) which correspond to the pointer coordinate positions within the effective range.

The arrows in FIGS. 3A, B, and C show the pointers as described above. The position coordinate of the mouse pointer in FIG. 3A is shown to be (167, 244) within the effective range P. Further, the position coordinate of the mouse pointer in FIG. 3B is shown to be (241, 254) within the effective range P and the position coordinate of the mouse pointer in FIG. 3C is shown to be (249, 255) within the effective range P.

In FIG. 3A, the gray-scale width (dynamic range) is set to 167-244. The background image of the latent fingerprint is actualized in this case, so that the latent fingerprint is unclear.

In FIG. 3B, the gray-scale width is set to 241-254, and the ridgeline shape of the latent fingerprint is more clarified in the region near the pointer compared to that of FIG. 3A.

Further, in FIG. 3C, the gray-scale width is set to 249-255, and the ridgeline shape of the latent fingerprint in the region including a character string "58b" that is the background image is clarified compared to that of FIGS. 3A and B. In the meantime, in the region near the pointer in FIG. 3C, there is a part where the ridgeline shape of the latent fingerprint is white and cannot be observed compared to that of FIG. 3B.

This makes it possible to set the appropriate dynamic range for actualizing the fingerprint ridgeline through performing the input operation by the operator to move the mouse 2 (perform right-drag in this case) even in the region where the ridgeline shape is latescent due to the influence of the background image and the like and the fingerprint ridgelines are hard to be observed.

The operator can clarify the latent fingerprint without transiting the operation screen or releasing the finger from the plot input button (left button of the mouse). Thus, through performing the input operation (specifically performing left-click of the mouse 2) for the clarified latent fingerprint, it is possible to input the minutia information quickly and easily.

As described above, it is possible with the fingerprint minutia input device 1 as the embodiment to clarify the fingerprint image suited for the positions on the pointer on the screen in a state where the plot operation can be done immediately (i.e., a state where a finger is placed on the left button, a state where left-click can be done) when the operator inputs the minutia positional information by using the mouse 2 for the fingerprint image outputted on the monitor 3 and at the same time makes the coordinate position of the pointer in the right-drag state corresponded to the gray-scale upper and lower values of the fingerprint image.

Further, the operator can adjust the output gray-scale value width of the fingerprint image through moving (right-dragging) the pointer while pressing the right button. Therefore, the operator can perform the plot operation of the minutiae in a display state in which the image region in the periphery of the position of the pointer the most clarified for the operator oneself (i.e., in a state where the visibility is the best for the operator).

Thereby, it is possible to speed up the minutia input operations and to effectively decrease the number of steps and the effort regarding the input operations of the minutia information done by the operator.

(Explanations Regarding Operations According to Embodiment)

Next, basic operations and entire operations regarding the content of the operations of the embodiment will be described.

First, the gray-scale value width adjustment unit 13 of the main device body 10 selects/sets the gray-scale intensity of the entire fingerprint image where the mouse pointer outputted/displayed on the display screen (monitor) 3 is located for gray-scale display within a range of the display gray-scale width constituted with the gray-scale upper limit value and the gray-scale lower limit value from the memory provided in advance according to an external command (a gray-scale intensity selecting/setting step).

Then, the gray-scale value width adjustment unit 13 converts the display position coordinate of the mouse pointer to the gray-scale upper limit value and the lower limit value and informs the gray-scale upper limit value and lower limit value to the image output controller 11 (a gray-scale value adjusting step).

Next, when setting/displaying the minutia display mark, the image output controller 11 updates/displays the output display of the fingerprint image with the display gray-scale width selected/set anew and sent by the gray-scale value width adjustment unit 13 (a gray-scale width update processing step).

Subsequently, when there is no new setting information of the display gray-scale width from the gray-scale value width adjustment unit 13, the set and displayed gray-scale width is fixed and held as the display gray-scale width for displaying and inputting the minutiae (a gray-scale width fixing/holding step).

Thereafter, the minutia input setting unit 12 sets/displays the minutia display marks on the minutiae of the fingerprint image fixedly displayed with the display gray-scale according to an external command (a fixed gray-scale width minutia inputting step/a display mark setting/displaying step).

Hereinafter, this will be described in more details by referring to the flowchart of FIG. 4.

First, it is assumed that a mouse pointer is displayed on the latent fingerprint image A outputted on the monitor 3. Here, it is assumed that the minutia input setting unit 12 inputs the minutia information according to a mouse operation (left click) of the operator and drawing is done (plotting is done) for showing the minutiae on the screen of the monitor 3 (FIG. 4: step S101).

When detecting that the right button of the mouse 2 (or a given key set in advance) is pressed down by the operator (FIG. 4: step S102), the gray-scale value width adjustment unit 13 starts the adjusting function of the gray-scale value width (dynamic range) (a gray-scale value width adjusting/starting function).

The gray-scale value width adjustment unit 13 sets the region (effective range region) having the prescribed length coordinate axes in the horizontal direction and the perpendicular direction on the monitor screen from a reference position by taking the position on the screen when right button is pressed down (right-clicked) (FIG. 4: step S103) as the reference position.

This effective range is defined as a region of an inside part (including the boundary) of a right triangle which is constituted with a longitudinal axis of a coordinate value from 0 as the reference position to 254 in the horizontal wide range direction, a lateral axis of a coordinate value from 255 as the reference position to 0 in the perpendicular direction, and a straight line having the lower end of the longitudinal axis and the right end of the lateral axis as its both ends. Further, within the region, each of the gray-scale lower value and the gray-scale upper value is defined to satisfy "gray-scale lower value<gray-scale upper value".

Figure 4:
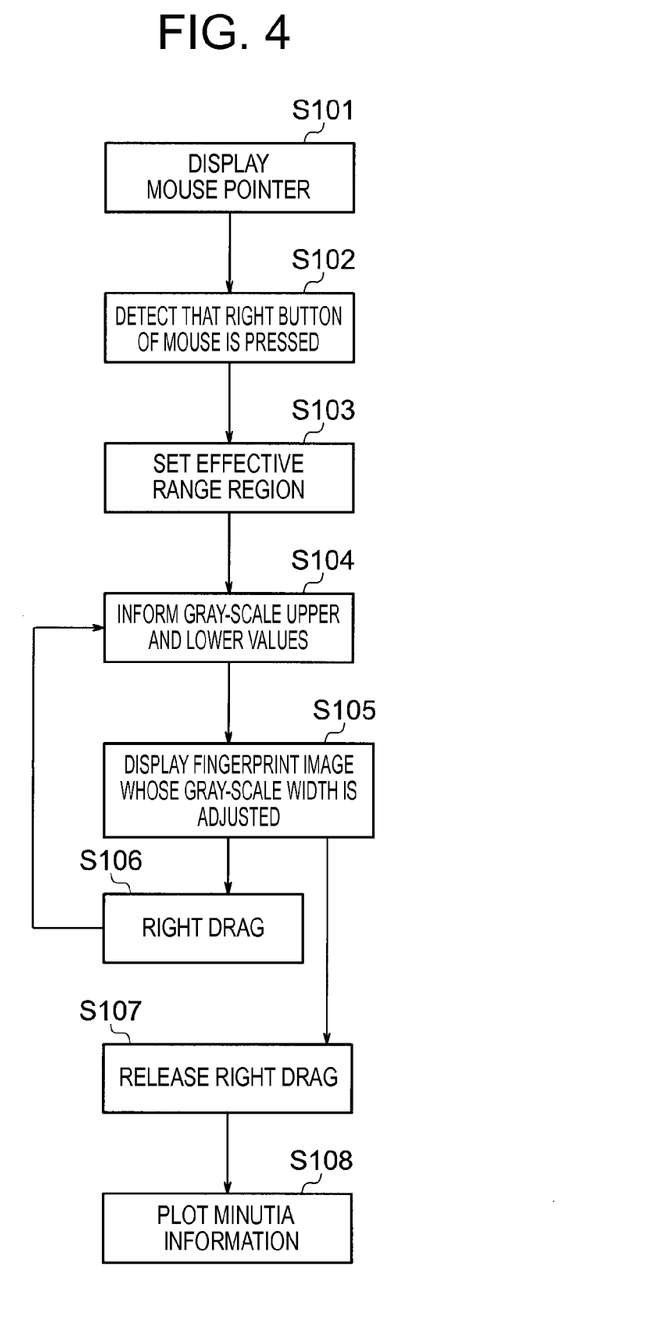
FIG. 4 is a flowchart showing operation processing steps executed by the fingerprint image minutia input device disclosed in FIG. 1.

Then, when an operation for moving the pointer on the screen of the monitor 3 within the effective range is executed in a right-drag state of the mouse 2, the gray-scale value width adjustment unit 13 informs the coordinate information within the effective range as the gray-scale upper value and the gray-scale lower value to the image output controller 11 (FIG. 4: step S104).

Note here that image output controller 11 outputs/displays the fingerprint image on the monitor 3 with the dynamic range in which the gray-scale upper value and the gray-scale lower value sent from the gray-scale value width adjustment unit 13 are taken as the upper limit value and the lower limit value (FIG. 4: step S105).

Thereby, the operator can change the dynamic range of the entire fingerprint image through moving the mouse pointer displayed on the monitor 3 within the effective range P through moving the mouse 2 by right-drag.

When the pointer (arrow) on the display screen of the monitor 3 moves within the effective range while the mouse 2 is in a right-drag state (FIG. 4: step S104), the gray-scale value width adjustment unit 13 determines each of the gray-scale upper value and the lower value corresponding to the position coordinate (position coordinate within the effective range P) of the mouse pointer (white arrow in FIG. 2) and transmits the gray-scale upper value and the lower value to the image output controller 11.

Then, the image output controller 11 outputs/displays the fingerprint image on the monitor 3 with the dynamic range (gray-scale width) having the gray-scale upper value and the lower value as the upper limit value and the lower limit value (FIG. 4: step S105).

Thereby, the operator can adjust the display dynamic range (display gray-scale range) of the latent fingerprint image outputted/displayed on the monitor 3 through moving (right-dragging) the mouse 2 while pressing the right button (FIG. 4: step S106).

Further, the image output controller 11 fixes the display dynamic range (display gray-scale value) of the fingerprint image outputted/displayed on the monitor 3 at the point when it is detected that the right-drag state is released (the right-button pressed state is released) (FIG. 4: step S107).

Note here that the operator can input the minutiae for the fingerprint image by performing left-click of the mouse 2 while the display gray-scale value of the fingerprint image is being fixed.

For example, through fixing the display gray-scale value (i.e., releasing the right-drag state) in a state where the latent fingerprint A in the region near the mouse pointer in the fingerprint image displayed on the monitor 3 is most clarified, the operator can perform a plotting operation of the minutiae in a state where the latent fingerprint is displayed with the highest visibility for the operator oneself.

Further, the operator plots the minutiae through performing left-click in the manner described above (FIG. 4: step S108).

Note here that execution contents of the gray-scale intensity selecting/setting step, the gray-scale value adjusting step, the gray-scale width update processing step, the gray-scale width fixing/holding step, the fixed gray-scale width minutia inputting step/the display mark setting displaying step, and each of other operation steps may be put into programs and structured to be executed by a computer provided to the main device body 10 or other computers.

In this case, the program may be recorded in a non-transitory recording medium such as a DVD, a CD, a flash memory, or the like. In that case, the program is read out from the recording medium and executed by the computer.

As described above, with the minutia input device 1 of the embodiment, the operator moves the pointer on the screen through performing right-drag in a state where left-click can be done at all times (in a state where a finger is placed on the left button), so that it is possible to perform the adjusting operation of the gray-scale width thereby.

This makes it possible for the operator to clarify the latent fingerprint in the image (latent fingerprint image) containing the latent fingerprint while performing input of the minutiae (without performing screen transition and the like), so that it is possible to effectively decrease the effort and the time required for the input operation of the minutiae. Further, it is also possible to effectively speed up the input operation of the minutiae for the latent fingerprint image done by the operator.

Regarding the embodiment described above, the new technical contents thereof can be summarized as follows. While a part of or a whole part of the embodiments can be summarized as follows as the new techniques, it is to be noted that the present invention is not necessarily limited only to the followings.

(Supplementary Note 1)

A fingerprint minutia input device including the main device body 10 which includes: the image output controller 11 which outputs/displays a fingerprint image containing fingerprint ridgelines and a pointer for designating a coordinate position of a minutia of the fingerprint image on the display screen (monitor) 3; and the minutia input setting unit 12 which sets/displays a minutia display mark for the minutia on the fingerprint image designated by the pointer according to an external command, wherein:
the main device body 10 includes the gray-scale value width adjustment unit 13 which sets gray-scale intensity of the entire fingerprint image where the pointer is located to be used for gray-scale adjustment within a display gray-scale range constituted with a gray-scale upper limit value and a gray-scale lower limit value according to an external command; and
the image output controller 11 includes a gray-scale width update function 11A which updates/outputs output display of the fingerprint image with the display gray-scale width set anew by the gray-scale value width adjustment unit 13 when setting/displaying the minutia display mark, and a gray-scale width fixing/holding function 11B which fixes and holds the set display gray-scale width as the display gray-scale width for displaying/inputting the minutia when there is no new setting information of the display gray-scale width from the gray-scale value width adjustment unit 13.

(Supplementary Note 2)

The fingerprint minutia input device as depicted in Supplementary Note 1, wherein:
the main device body 10 includes the setting information transfer unit 14 which includes a first transfer processing function which, when coordinate positional information of a moved destination of the pointer on the fingerprint image is externally inputted via an input apparatus (e.g., mouse), sends it to the image output controller 11, and a second transfer processing function which, when gray-scale intensity information regarding the display gray-scale width in which the upper limit value and the lower limit value of the gray-scale intensity for displaying the image are specified is set via the input apparatus (e.g., mouse), sends it to the gray-scale value adjustment unit; and
the setting information transfer unit 14 includes a third transfer processing function which, when a display command for the minutia on the fingerprint image is externally inputted to the minutia input setting unit 12 (e.g., by using a mouse or a keyboard) while the gray-scale intensity information is being inputted/set, performs transfer processing of the minutia display command to the minutia input setting unit 12.

(Supplementary Note 3)

The fingerprint minutia input device as depicted in Supplementary Note 2, wherein the image output controller 11 updates/displays an output display of the fingerprint image with the display gray-scale width set anew by the gray-scale value width adjustment unit 13 by starting the gray-scale width update function 11A at a timing of input of a minutia display command when the minutia display command from an operation command transfer unit for the minutia input setting unit is inputted, and fixedly sets/controls the display gray-scale width regarding the updated display by starting the gray-scale width fixing/holding function 11B when the input of the minutia display command is released.

(Supplementary Note 4)

The fingerprint minutia input device as depicted in Supplementary Note 3, wherein:
the gray-scale value width adjustment unit 13 includes a gray-scale value memory 13A which stores a plurality of stages of gray-scale lower limit values in which values of the gray-scale lower limit values of the fingerprint image change successively and a plurality of stages of gray-scale upper limit values in which values of the gray-scale upper limit values of the fingerprint image change successively; and
in the gray-scale value memory 13A, a plurality of stages of each of the lower limit values for the single upper limit value is stored in a continuously and successively selectable manner in response to an external command.

(Supplementary Note 5)

The fingerprint minutia input device as depicted in any one of Supplementary Notes 2 to 4, wherein:
the input apparatus is constituted with the mouse 2 including the left click part 2a and the right click part 2b which are press button switches;
the left click part 2a of the mouse 2 includes a display command input function 2A which externally inputs a minutia display mark setting command for the minutia input setting unit 12 through a click operation of the left click part 2a; and
the right click part of the mouse includes a gray-scale display range setting function 2B which sets/inputs the upper limit value and the lower limit value for displaying the gray-scale of the fingerprint image for the gray-scale value width adjustment unit 13 by a click operation of the right click part through performing successive selection while moving the mouse.

(Supplementary Note 6) (Invention of Method)

A fingerprint minutia input method used for the fingerprint minutia input device including the main device body 10 which includes the image output controller 11 which outputs/displays a fingerprint image containing fingerprint ridgelines and a pointer for designating a coordinate position of a minutia of the fingerprint image on the display screen (monitor) 3 and the minutia input setting unit 12 which sets/displays a minutia display mark for the minutia on the fingerprint image designated by the pointer according to an external command, and the method includes:

- selecting and setting gray-scale intensity of the entire fingerprint image where the pointer is located to be used for gray-scale display within a display gray-scale range constituted with a gray-scale upper limit value and a gray-scale lower limit value from a memory provided in advance by the gray-scale value width adjustment unit 13 of the main device body 10 according to an external command (a gray-scale intensity selecting/setting step);
- then, updating/outputting output display of the fingerprint image by the image output controller 11 with the display gray-scale width set anew by the gray-scale value width adjustment unit 13 when setting/displaying the minutia display mark (a gray-scale width update processing step);
- subsequently, fixing and holding the set display gray-scale width as the display gray-scale width for displaying/ inputting the minutia when there is no new setting information of the display gray-scale width from the gray-scale value width adjustment unit 13 (a gray-scale width fixing/holding step); and
- thereafter, setting/displaying the minutia display mark for the minutia of the fingerprint image fixedly set with the display gray-scale width by the minutia input setting unit 12 according to an external command (a display mark setting/displaying step).

(Supplementary Note 7) (Program Invention)

A fingerprint minutia input program used for the fingerprint minutia input device including the main device body 10 which includes the image output controller 11 which outputs/displays a fingerprint image containing fingerprint ridgelines and a pointer for designating a coordinate position of a minutia of the fingerprint image on the display screen (monitor) 3 and the minutia input setting unit 12 which sets/displays a minutia display mark for the minutia on the fingerprint image designated by the pointer according to an external command, and the program causes a computer provided to the main device body 10 to execute each of:

- a display gray-scale value acquiring function which selectively takes out gray-scale intensity of the entire fingerprint image where the pointer is located to be used for gray-scale display within a display gray-scale range constituted with a gray-scale upper limit value and a gray-scale lower limit value from a memory provided in advance additionally according to an external command;
- a gray-scale width updating/displaying function which updates/outputs output display of the entire fingerprint image with the display gray-scale width selected anew when setting/displaying the minutia display mark;
- a gray-scale width fixing/holding function which fixes and holds the set display gray-scale width as the display gray-scale width for displaying/inputting the minutia when there is no new setting information of the display gray-scale width; and
- a display mark setting processing function which sets/ displays a display mark for the minutia of the fingerprint image fixedly set with the display gray-scale width according to an external command.

This application claims the Priority right based on Japanese Patent Application No. 2012-116565 filed on May 22, 2012 and the disclosure thereof is hereby incorporated by reference in its entirety.

INDUSTRIAL APPLICABILITY

The present invention can be effectively applied to the minutia input system which performs input operations of the minutia information for a display screen of a tablet terminal and for a touch panel display of a touch panel device.

REFERENCE NUMERALS

1 Minutia information input device
2 Input apparatus (mouse)
2A Display command inputting function
2B Gray-scale display range setting function
3 Data display module (display screen/monitor)
10 Main device body
10A Master controller
11 Image output controller
11A Gray-scale width update function
11B Gray-scale width fixing/holding function
12 Minutia input setting unit
13 Gray-scale value width adjustment unit
13A Gray-scale value memory
14 Setting information transfer unit
15 Memory unit
21 Input apparatus (keyboard)

The invention claimed is:

1. A fingerprint minutia input device comprising a main device body, the fingerprint minutia input device comprising:
   a memory storing computer program instructions; and
   a processor configured execute the compute program instructions to:
      output a fingerprint image containing fingerprint ridgelines and a pointer for designating a coordinate position of a minutia of the fingerprint image on a display screen;
      set, based on an external command, a minutia display mark for the minutia on the fingerprint image designated by the pointer;
      set, based on an external command, a gray-scale intensity of the entire fingerprint image where the pointer is located, the gray-scale intensity being adjustable within a display gray-scale range between a gray-scale upper limit value and a gray-scale lower limit value;
      update a width of the display gray-scale with the fingerprint image when setting the minutia display mark; and
      hold the display gray-scale width for outputting the minutia when no new setting information of the width of the display gray-scale is received.

2. The fingerprint minutia input device as claimed in claim 1, wherein the processor is further configured to execute the instructions to:

send coordinate positional information of a moved destination of the pointer on the fingerprint image when the coordinate positional information is externally inputted via an input apparatus, send new setting information for the width of the display gray-scale, the setting information specifying the upper limit value and the lower limit value, when the gray-scale intensity; and perform, when the display command for the minutia on the fingerprint image is externally input, transfer processing of a minutia display command while the gray-scale intensity is being set.

3. The fingerprint minutia input device as claimed in claim 2, wherein the processor is further configured to execute the instructions to:

output, or update output of, the fingerprint image with the display gray-scale width set anew by starting updating of the width of the display gray-scale at a timing of input of a minutia display command when the minutia display command is inputted, and fixedly set the display gray-scale width regarding the updated display by starting the gray-scale width holding when the input of the minutia display command is released.

4. The fingerprint minutia input device as claimed in claim 3, wherein the input device further comprises:

a gray-scale value memory which stores a plurality of stages of gray-scale lower limit value stages, where in each lower limit value stage, the gray-scale lower limit values change successively, and a plurality of gray-scale upper limit value stages, where in each upper limit stage, the gray-scale upper limit values change successively; and wherein a plurality of stages is stored to be continuously and successively selectable in response to an external command.

5. The fingerprint minutia input device as claimed in claim 2, wherein:

the input apparatus includes a mouse comprising a left click part and a right click part;

operation of the left click part of the mouse provides a display command which externally inputs a minutia display mark setting command; and successive operation of the right click part while moving the mouse provides a gray-scale display range setting which sets the upper limit value and the lower limit value for displaying the gray-scale of the fingerprint image.

6. A fingerprint minutia input method using a fingerprint minutia input device comprising a main device body which outputs a fingerprint image containing fingerprint ridgelines and a pointer for designating a coordinate position of a minutia of the fingerprint image on a display screen, and which sets a minutia display mark for the minutia on the fingerprint image designated by the pointer according to an external command, the method comprising:

setting, based on an external command, a gray-scale intensity of the entire fingerprint image where the pointer is located, the gray-scale intensity being adjustable within a display gray-scale range between a gray-scale upper limit value and a gray-scale lower limit value from a memory;

updating a width of the display gray-scale with the fingerprint image when setting the minutia display mark;

holding the display gray-scale width for outputting the minutia when no new setting information of the width of the display gray-scale is received; and displaying the set minutia display mark for the minutia of the fingerprint image according to an external command.

7. A non-transitory computer readable recording medium storing a fingerprint minutia input program for a fingerprint minutia input device comprising a main device body which outputs a fingerprint image containing fingerprint ridgelines and a pointer for designating a coordinate position of a minutia of the fingerprint image on a display screen, and which sets a minutia display mark for the minutia on the fingerprint image designated by the pointer according to an external command, the program, when executed by a processor of the fingerprint minutia input device, causes the processor to:

selectively reduce gray-scale intensity of the entire fingerprint image where the pointer is located, the gray-scale intensity being within a display gray-scale range between a gray-scale upper limit value and a gray-scale lower limit value from a memory;

update a width of the display gray-scale with the entire fingerprint image when setting the minutia display mark;

hold the display gray-scale width for outputting the minutia when no new setting information of the width of the display gray-scale received; and display the set minutia display mark for the minutia of the fingerprint image according to an external command.

8. The fingerprint minutia input device as claimed in claim 1, wherein the processor is further configured to execute the instructions to:

superimpose an effective range region defining the gray-scale upper limit value and a gray-scale lower limit value on the fingerprint image.

9. The fingerprint minutia input device as claimed in claim 1, wherein the processor is further configured to execute the instructions to:

plot, based on the updated width of the display gray-scale, a clarified image region in the periphery of the pointer within the output fingerprint image.

10. The fingerprint minutia input method as claimed in claim 6, wherein the method further comprises:

sending coordinate positional information of a moved destination of the pointer on the fingerprint image when the coordinate positional information is externally inputted via an input apparatus, sending new setting information for the width of the display gray-scale, the setting information specifying the upper limit value and the lower limit value, when the gray-scale intensity is set via the input apparatus; and performing, when the display command for the minutia on the fingerprint image is externally input, transfer processing of a minutia display command while the gray-scale intensity is being set.

11. The fingerprint minutia input method as claimed in claim 10, wherein the method further comprises:

outputting, or updating output of, the fingerprint image with the display gray-scale width set anew by starting updating of the width of the display gray-scale at a timing of input of a minutia display command when the minutia display command is inputted, and fixedly setting the display gray-scale width regarding the updated display by starting the gray-scale width holding when the input of the minutia display command is released.

12. The fingerprint minutia input method as claimed in claim 11, wherein the method further comprises:
   storing a plurality of gray-scale lower limit value stages, where in each lower limit value stage, the gray-scale lower limit values change successively; and
   storing a plurality of gray-scale upper limit value stages, where in each upper limit stage, the gray-scale upper limit values change successively; wherein
   a plurality of stored stages is continuously and successively selectable in response to an external command.

13. The fingerprint minutia input method as claimed in claim 10, wherein the method further comprises:
   providing a display command which externally inputs a minutia display mark setting command via operation of a left click part of a mouse; and
   providing a gray-scale display range setting which sets the upper limit value and the lower limit value for displaying the gray-scale of the fingerprint image via successive operation of a right click part of a mouse while moving the mouse.

14. The fingerprint minutia input method as claimed in claim 6, wherein the method further comprises:
   superimposing an effective range region defining the gray-scale upper limit value and the gray-scale lower limit value on the fingerprint image.

15. The fingerprint minutia input method as claimed in claim 6, wherein the method further comprises:
   plotting, based on the updated width of the display gray-scale, a clarified image region in the periphery of the pointer within the output fingerprint image.

16. The non-transitory computer readable recording medium as claimed in claim 7, wherein the processor is further caused to:
   send coordinate positional information of a moved destination of the pointer on the fingerprint image when the coordinate positional information is externally inputted via an input apparatus, and
   send new setting information for the width of the display gray-scale, the setting information specifying the upper limit value and the lower limit value, when the gray-scale intensity is set via the input apparatus; and
   perform, when the display command for the minutia on the fingerprint image is externally input, transfer processing of a minutia display command while the gray-scale intensity is being set.

17. The non-transitory computer readable recording medium as claimed in claim 16, wherein the processor is further caused to:
   output, or update output of, the fingerprint image with the display gray-scale width set anew by starting updating of the width of the display gray-scale at a timing of input of a minutia display command when the minutia display command is inputted, and
   fixedly set the display gray-scale width regarding the updated display by starting the gray-scale width holding when the input of the minutia display command is released.

18. The non-transitory computer readable recording medium as claimed in claim 17, wherein the processor is further caused to:
   store a plurality of gray-scale lower limit value stages, where in each lower limit value stage, the gray-scale lower limit values change successively; and
   store a plurality of gray-scale upper limit value stages, where in each upper limit stage, the gray-scale upper limit values change successively; wherein
   a plurality of stored stages is continuously and successively selectable in response to an external command.

19. The non-transitory computer readable recording medium as claimed in claim 16, wherein the processor is further caused to:
   provide a display command which externally inputs a minutia display mark setting command via operation of a left click part of a mouse; and
   provide a gray-scale display range setting function which sets the upper limit value and the lower limit value for displaying the gray-scale of the fingerprint image via successive operation of a right click part of a mouse while moving the mouse.

20. The non-transitory computer readable recording medium as claimed in claim 7, wherein the processor is further caused to:
   superimpose an effective range region defining the gray-scale upper limit value and a gray-scale lower limit value on the fingerprint image.

* * * * *